United States Patent [19]

Bushberger

[11] Patent Number: 5,267,579
[45] Date of Patent: Dec. 7, 1993

[54] OSCILLATING FLOSSING IMPLEMENT

[76] Inventor: Todd E. Bushberger, S72 W13839 Woods Rd., Muskego, Wis. 53150

[21] Appl. No.: 542,448

[22] Filed: Jun. 22, 1990

[51] Int. Cl.$^5$ .............................................. A61C 15/00
[52] U.S. Cl. ................................... 132/322; 132/323; 15/22.1
[58] Field of Search .................. 132/322, 323; 15/22.1

[56] References Cited

U.S. PATENT DOCUMENTS

| | | |
|---|---|---|
| 618,009 | 1/1989 | LaVarre . |
| 1,171,177 | 2/1916 | De L'Eau . |
| 1,184,052 | 5/1916 | Turner et al. . |
| 1,480,101 | 1/1924 | Ogden . |
| 2,187,442 | 1/1940 | Beach ................................ 132/92 |
| 2,282,700 | 5/1942 | Bobbroff ............................ 15/22 |
| 3,138,813 | 6/1964 | Kaplan .............................. 15/22.1 |
| 3,183,538 | 5/1965 | Hubner .............................. 15/22.1 |
| 3,196,299 | 7/1965 | Kott .................................. 15/22.1 |
| 3,421,524 | 1/1969 | Waters ............................... 132/92 |
| 3,534,745 | 10/1970 | Waters ............................... 132/322 |
| 3,759,274 | 9/1973 | Warner ............................... 132/92 |
| 3,835,872 | 9/1974 | Daniel ................................ 132/92 |
| 3,858,594 | 1/1975 | Ensminger .......................... 132/325 |
| 3,882,879 | 5/1975 | Lucas ................................ 132/325 |
| 4,265,257 | 5/1981 | Salyer ................................ 132/91 |
| 4,338,957 | 7/1982 | Meibauer ............................ 132/91 |
| 4,458,702 | 7/1984 | Grollimund ......................... 132/322 |
| 4,586,521 | 5/1986 | Urso ................................. 132/92 |
| 4,605,025 | 8/1986 | McSpadden ......................... 132/92 |
| 4,660,584 | 4/1987 | Wofford ............................. 132/325 |
| 4,706,695 | 11/1987 | Urso ................................. 132/92 |
| 4,830,032 | 5/1989 | Jousson ............................. 132/323 |
| 5,002,487 | 3/1991 | Tichy ................................ 15/22.1 |
| 5,016,660 | 5/1991 | Boggs ................................ 132/323 |

*Primary Examiner*—Gene Mancene
*Assistant Examiner*—Frank A. LaViola
*Attorney, Agent, or Firm*—Michael, Best & Friedrich

[57] ABSTRACT

A flossing implement including a hollow handle, a pair of fingers extending from the handle to support therebetween a strand of dental floss, and an electric motor in the handle carrying an eccentric weight for vibrating the handle and, through the handle, a strand of dental floss supported at the end of the handle.

23 Claims, 2 Drawing Sheets

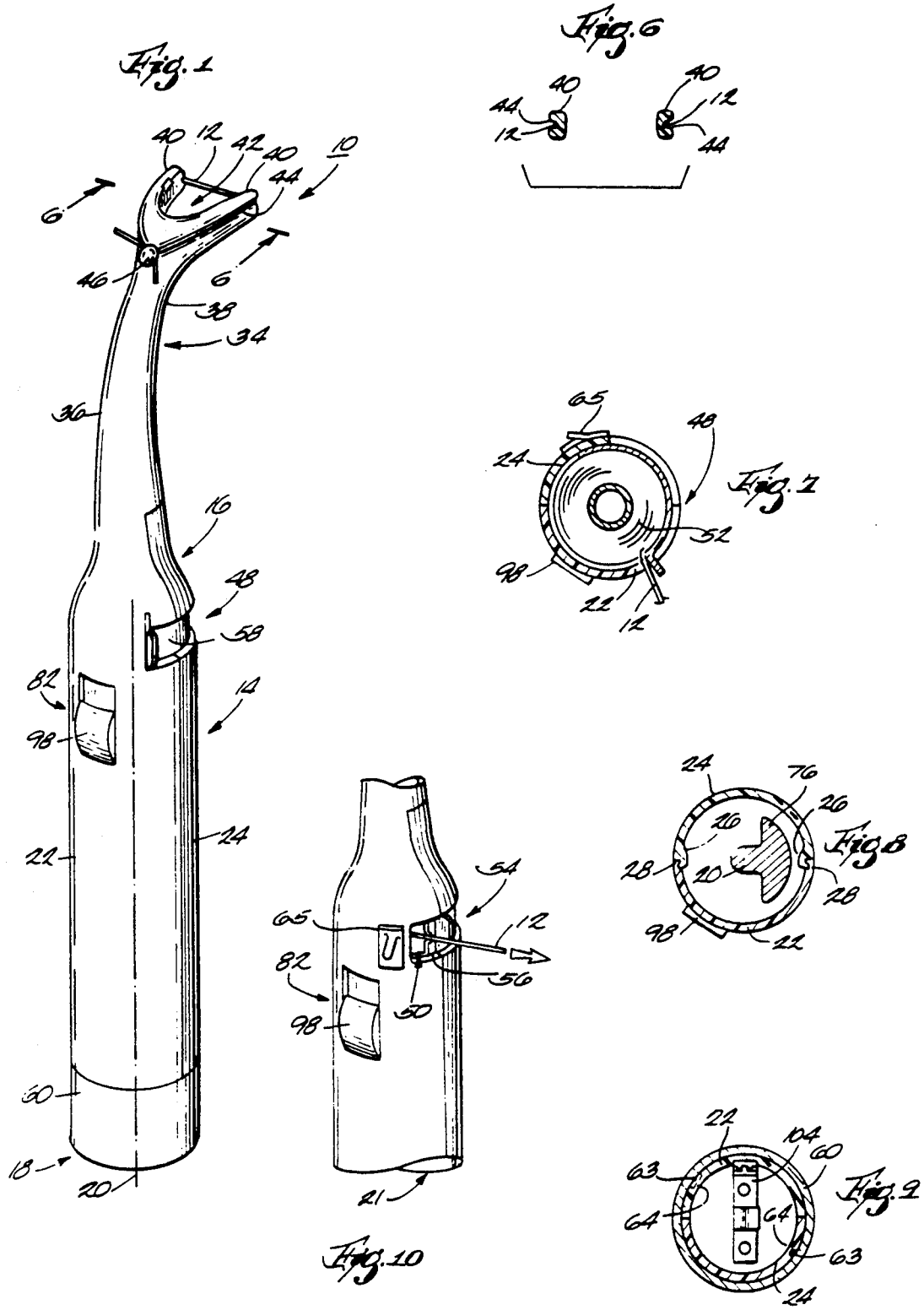

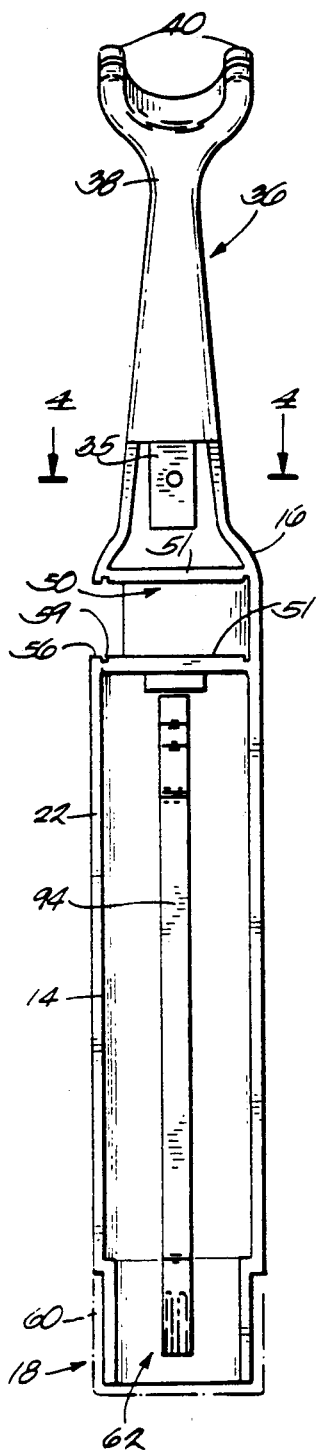

OSCILLATING FLOSSING IMPLEMENT

BACKGROUND OF THE INVENTION

The invention relates generally to implements for dental hygiene and more specifically to dental flossing implements.

Dental flossing is a well known technique for promoting dental hygiene and for preventing tooth decay and gum disease. Commonly, dental floss is held in two hands between the thumbs and forefingers and moved in a reciprocating motion over opposing surfaces between a pair of teeth. Often, effective cleaning by the floss of the opposing surfaces between the teeth is made difficult because of the difficulty in placing the floss between the teeth For example, it may be difficult with the dental floss in both hands to reach into the back of the mouth to place the strand of dental floss between a pair of molars. Also, it is difficult to insert the floss between teeth that are tightly spaced, i.e. have very little space therebetween. Because of the difficulty in placing the floss between the teeth, it may also be difficult to properly move the floss to effectively clean between the teeth.

In the prior art, it is known to support a strand of floss on a flossing implement to aid in locating the floss between teeth in the back of the mouth. It is also known in the prior art to provide means associated with the implement for imparting a reciprocating motion to the floss itself, or for imparting a reciprocating motion to a portion of the flossing implement. Reciprocating motion, in the prior art, consisted of moving the length of floss in the direction of its longitudinal extension in a back and forth manner. Such prior art flossing implements have relatively complex designs and can present difficulty because of the bulk of the implement itself.

It is therefore an object of this invention to provide a flossing implement which aids in the cleaning of surfaces between the teeth.

It is another object of this invention to provide a flossing implement which aids in the placement of a strand of floss between a pair of teeth.

It is a further object of this invention to provide a flossing implement having a simple design for holding a strand of dental floss and for vibrating the strand of dental floss.

SUMMARY OF THE INVENTION

In order to accomplish these and other objects, this invention provides a flossing implement adapted to support a strand of dental floss. The implement includes a handle which can be easily held in one hand and which is formed to aid in the proper use of the floss. The flossing implement includes a pair of fingers extending from one end of the handle to hold a strand of dental floss extending, in tension, between the fingers. The fingers are grooved and adapted to securely retain the strand of floss so that the strand of floss extends between the fingers and is substantially taut. Preferably, the pair of fingers extend from a gently curved neck portion of the handle and are formed, with the neck portion, so as to facilitate the positioning of the relatively taut strand of floss between a pair of teeth. Due to the curvature of the neck and the clearance provided between the pair of fingers, the flossing implement allows the user to easily position the strand of floss in the space between a pair of molars in the back of the mouth, as well as between teeth in the front of the mouth.

In order to aid in the effective cleaning between the teeth, the flossing implement includes means to vibrate through the handle to the fingers and the strand of floss As a result of imparting a vibratory motion to the strand of floss, the floss can be easily slipped between even tightly spaced teeth. Preferably, operation of a thumb actuable switch allows the user of the flossing implement to activate a battery-powered electric motor which is housed in the handle and which, when turned on, rotates an eccentric weight supported on the motor shaft inside the handle. Rotation of the eccentric weight causes vibration of the handle and, through it, vibration of the strand of floss. The flossing implement thus allows the user to properly position the strand of floss, with one hand, at or between a pair of teeth anywhere in the mouth. Further, once the strand of floss is positioned as desired, the user can slip the floss between the selected teeth and impart a vibratory motion to the strand of floss for cleaning between the pair of teeth. If the teeth are tightly spaced the vibratory motion can be imparted to the floss strand to assist in sliding it between the teeth.

The flossing implement also provides a storage compartment for a supply of floss. Preferably, the storage compartment is in the handle and is adapted to house a spool of floss for ready access. When a new length of floss is needed, floss is unwound from the storage compartment and a desired length of floss is cut using a suitable cutting surface preferably included as part of the flossing implement. The length of floss is then secured across the outer ends of the fingers.

The invention thus provides a flossing implement which has a relatively narrow construction to facilitate placement of a strand of dental floss between a pair of teeth. The flossing implement uses a simple design having a minimum of moving parts to impart vibratory motion to the floss The implement is compact, yet self-contained as it houses the electric motor, a source of operating power for the motor, and a supply of dental floss.

Various other features and advantages of the invention will become apparent to one skilled in the art upon review of the following detailed description, drawings, and claims

DESCRIPTION OF THE DRAWINGS

FIG. 1 is a perspective view of a flossing implement embodying various features of the invention.

FIG. 2 is an elevation view of a portion of the flossing implement shown in FIG. 1.

FIG. 3 is an elevation view of a portion of the flossing implement shown in FIG. 1.

FIG. 4 is a cross-sectional view of an assembled flossing implement taken along line 4—4 in FIG. 2.

FIG. 5 is a cross-sectional view of an assembled flossing implement taken along line 5—5 in FIG. 3.

FIG. 6 is a cross-sectional view of the flossing implement shown in FIG. 1 and taken along line 6—6.

FIG. 7 is a cross-sectional view of an assembled flossing implement and taken along line 7—7 in FIG. 3.

FIG. 8 is a cross-sectional view of an assembled flossing implement taken along line 8—8 in FIG. 3.

FIG. 9 is a cross-sectional view of an assembled flossing implement and taken along 9—9 in FIG. 3.

FIG. 10 is an enlarged view of a portion of the flossing implement shown in FIG. 1.

Before one embodiment of the invention is explained in detail, it is to be understood that the invention is not limited in its application to the details of construction and the arrangements of components set forth in the following description or illustrated in the drawings The invention is capable of other embodiments and of being practiced or carried out in various ways. Also, it is to be understood that the phraseology and terminology used herein is for the purpose of description and should not be regarded as limiting.

DETAILED DESCRIPTION OF THE INVENTION

FIG. 1 illustrates a flossing implement 10 adapted for use with a standard filament or strand of dental floss 12. The flossing implement 10 includes an elongated handle 14 having opposite ends 16, 18 and a longitudinal axis 20 extending between the opposite ends 16, 18. The handle 14 is substantially hollow and defines therein (FIG. 10) a cavity, or interior space 21 extending substantially from end 16 of the handle to the other opposite end 18. The handle 14 is generally cylindrical and is sized to fit comfortably in the hand of the user.

For ease of assembly, the flossing implement 14 includes (FIG. 2) a first semi-cylindrical shell 22 and (FIG. 3) a second semi-cylindrical shell 24. As shown in FIG. 8, the second shell 24 has a plurality of tabs 26 which extend from the edges of the second shell 24 and which, when assembled with the first shell 22, engage and interlock with a plurality of corresponding grooves 28 in the edges of the first shell 22 to align the first and second shells for assembly.

The flossing implement also includes means 30 for selectively fastening the first and second shells 22, 24 together. In the preferred embodiment (FIG. 4), the selective fastening means 30 includes a screw 32 or some similar fastener which extends through a portion 33 of the second shell 24 and threads into a corresponding portion 35 of the first shell 22. As described below, it is contemplated that the user will not be required to disassemble the shells 22, 24 on a regular basis as other means to allow access to the cavity 21 are provided.

The handle 14 includes means 34 extending from one opposite end 16 for supporting a strand of dental floss. Preferably, the means 34 is capable of holding the dental floss 12 in tension, that maintains the floss taut to facilitate positioning the floss between a pair of teeth for cleaning the teeth. The means 34 for supporting the dental floss includes a neck portion 36 which extends from the one end 16 of the handle 14 generally parallel to or in the direction of the axis 20 of the handle. The neck portion 36 is relatively slender and generally cylindrical, and has a diameter which tapers from a diameter substantially equal to the diameter of the cylindrical handle 14 at the one end 16 to a smaller diameter at the end 38 of the neck portion 36. The neck portion 36 extends generally parallel to the axis along a major portion of its length but the tapered end 38 bends away, or diverges from the axis 20. Structurally, the tapered end 38 terminates in a pair of spaced-apart fingers 40 which diverge from the neck portion 36, and axis 20, to define therebetween a generally V-shaped space 42 and which extends generally transverse to or substantially perpendicularly to the axis 20. The combination of a slender neck portion and a diverging pair of fingers provides an end portion which extends laterally of the general body of the implement to allow the user to reach into the mouth and move the floss upwardly or downwardly into position between a pair of teeth.

Each of the spaced-apart fingers 40 includes a groove 44 (FIG. 6) which extends around the outside of each finger and which is adapted to receive the strand of floss. The neck portion 36 also supports a knob 46 located adjacent the end 38 and adjacent the inner ends of the pair of fingers 40. The knob is adapted to secure the strand of floss 12 by winding the strand of floss 12 around the knob 46. In the preferred embodiment, it is contemplated that one end of the strand of floss 12 is wrapped around the knob 46 to secure the strand of floss to the handle. The strand 12 is seated in the groove 44 in a finger 40 and wraps around the finger, extends across the space 42 between the two fingers, and wraps around the other of the fingers 40 in the groove 44 of the other finger. The other end of the strand 12 is wound around the knob 46 t securely fasten the strand of floss in tension across the V-shaped space 42.

The fingers 40 are sufficiently spaced-apart to provide clearance on either side of a row of teeth when the floss is placed between the teeth, but are sufficiently close together to facilitate positioning of the neck portion 36 and the fingers 40 into the mouth and to position the strand of floss 12 between a pair of teeth. Preferably, the space between the fingers 40 is about ¾ inch and the dimension from the outer surface of one of the fingers to the outer surface of the other finger is about 1 inch. Provision of the easily-held, cylindrical handle 14, a curved and tapered neck portion 36 terminating in the spaced-apart fingers 40, and means 46 for holding the floss in a relatively taut position, allows the user of the flossing implement 10 to position the strand of floss 12 between a pair of teeth using only one hand, and thus facilitates the positioning of the strand of floss between a pair of teeth; for example, a pair of molars in the back of the mouth. Holding the floss at the outer ends of fingers that extend laterally from the general longitudinal exterior of the handle facilitating easy positioning of floss between teeth including rear molars.

The handle 14 also includes means 48 for storing a supply of floss. The means 48 for storing a supply of floss includes a storage compartment 50 in the cavity 21 of the handle. As shown in FIGS. 2 and 3, the handle 14 includes a pair of inwardly extending walls 51 which partition a portion of the cavity 21 into a storage compartment 50 adapted to support therein a spool 52 of floss.

As mentioned above, the handle 14 also includes means 54 providing access to the cavity 21. This includes a first opening 56 extending radially around the circumference of the assembled handle and communicating with the storage compartment 50 and providing access to the spool of floss 52. In the illustrated embodiment (FIG. 1) the first opening 56 extends around the assembled handle 14 to include a portion of the first shell 22 and a portion of the second shell 24. As shown in FIG. 7, the first opening 56 extends less than one-half of the circumference of the handle 14 for reasons explained below.

A slidable door 58 is provided to open and close the first opening 56. The slidable door 58 is disposed in a groove 59 which extends radially around the circumference of the handle. The door 58 is slideable to open and close the first opening 56, but is limited in its travel to less than half of the circumference of the handle, as shown in FIG. 7. Because the first opening 56 is less than the diameter of the spool, the restricted opening of the door 58 prevents the spool of floss 52 from falling out of the storage compartment 50 when the door 58 is completely open. In order to periodically replace an empty spool of floss in the storage compartment, it is contemplated that the user will disassemble the handle 14 by removing the fastener 32 and separating the first and second shells 22, 24.

The means 54 for affording access to the cavity 21 in the handle 14 also includes a removable end cap 60 which is supported on the other opposite end 18 of the handle 14. The end cap 60 closes a second opening 62 to the cavity 21 and provides, as fully described below, access to the cavity 21 for placing a battery in the interior of the handle. The end cap 60 can be threaded or snapped on to end 18 of the handle 14. In the illustrated embodiment, the end cap 60 is slipped onto end 18 of the handle 14 and held in place by a friction fit. As shown in FIG. 9, and for reasons fully discussed below, the inner wall of the cap 60 has a pair of keys 63 which engage slots 64 in the outer wall of the handle so as to assure proper orientation of the end cap 60 on the handle 14.

The flossing implement 10 also includes means including a metal shearing element 65 supported on the outside of the handle 14 adjacent the first opening 56 for cutting the floss. After a strand of floss has been unwound from the spool 52 by pulling the strand of floss through the door 58, the strand can be cut to length by using the shearing element 65. The flossing implement 10 thus allows the user to unwind a strand of floss from the spool 52 and cut the floss to length whenever a new strand of floss is required.

In order to aid in the effective cleaning of the teeth, the flossing implement 10 also includes eccentric oscillating means 66 in the cavity 21 for vibrating the handle 14. The eccentric oscillating means 66 includes an electric motor 68 housed in the cavity 21 and securely held in position by a plurality of inwardly extending projections 70 which engage the casing 72 of the electric motor 68. The electric motor 68 has a rotatable spindle 74 which extends along the axis 20 of the handle 14 and which carries an eccentric weight 76 for rotation of the weight 76 about the axis 20. In the illustrated embodiment, a bearing support 78 projects inwardly from the walls of the handle 14 to provide bearing support for the spindle 74 and additional support to secure the motor 68 in position. As shown in FIG. 8, the spindle 74 supports the weight 76 so that the center of mass of the weight 76 is spaced from the axis 20 of the handle, which is also the axis of rotation. Eccentric rotation of the weight 76 around the axis 20 causes vibration of the handle 14, through it vibration of spaced-apart fingers 40 and through the fingers vibration of the floss 12 held thereby. The fact the floss is supported at the end of an elongated handle accentuates the vibratory motion of the floss. That is, since the fingers supporting the floss are at the end of an elongated handle the vibrating motion imparted by the rotating eccentric weight increases as it progresses out to the free end of the handle.

The electric motor 68 is operably connected to a source of current 80 by user actuable switch means 82 for controlling operation of the motor 68 and for selectively connecting the motor 68 with the source of current 80. In the preferred embodiment, the source of current 80 is a battery 84 housed by the handle 14. Preferably, the battery 84 can be placed into the interior of the handle in a space adjacent the electric motor 68 by means of the second opening 62. In the preferred embodiment of the flossing implement 10, a single, AA size battery serves as the source of current for the electric motor 68.

The user actuable switch means 82 completes a circuit from one pole 86 of the battery 84 to a motor lead 88 and from the other pole 90 of the battery 84 to a second lead 92 of the motor 68. In the illustrated embodiment, the motor casing 72 is made of metallic conductor and serves as the first lead 88 for the motor 68. The switch means 82 includes a metallic strip 94 which is supported on the interior of the first shell 22 and extends from a point adjacent the metal casing 72 to the end 18 of the handle 14 adjacent the second opening 62. The strip 94 includes a detent 96 (FIG. 5) at the end of the strip 94 adjacent the metal casing 72 which can be biased into contact with the casing 72.

The switch means 82 also includes a user actuable thumb switch 98 which is supported by the first shell 22 and which extends outwardly from the outer surface of the first shell 22, and which includes (FIG. 5) an inwardly extending projection 100. The thumb switch 98 is selectively movable between an "on" position and an "off" position. In the "off" position, as shown in FIG. 5, the inwardly extending projection 100 engages the detent 96 in the metal strip 94 and allows the metal strip 94 to move to a position spaced away from the motor casing 72. When in the "on" position, the inwardly extending projection 100 moves out of engagement with the detent 96 and moves the end of the strip 94 inwardly of the cavity 21 and into contact with the motor casing 72.

The switch means 82 also includes a contact spring 102 disposed on the inside of the end cap 60 and extending into contact with the first pole 86 of the battery 84. The spring 102 can be in the form of a flexing metal strip (FIG. 3). The spring 102 extends along the inner wall of the end cap (FIG. 9) in the form of a contact 104 to engage the end of the metal strip 94. As best shown in FIG. 5, and as mentioned above, the contact 104 in the end cap 60 engages the end of the metal strip 94 to complete one half of the circuit between the casing 72 of the electrical motor 68 and a pole 86 of the battery. Because of the keyed relationship between the handle 14 and the end cap 60 described above, the proper orientation between the contact 104 and the metal strip 94 is assured and maintained.

The switch means 82 also includes a second lead 92 (FIG. 3), extending from the electrical motor 68 to a contact plate 108. The contact plate 108 is supported by a contact plate support 110 which extends inwardly from the second shell 24 to support the contact plate 108 between the electrical motor 68 and the other pole 90 of the battery 84. The contact spring 102 supported by the end cap 60 biases the battery 84 into engagement with the contact plate 108, thus closing the second half of the circuit between the other pole 90 of the battery 84 and the second lead 92 of the electrical motor 68.

In operation, the user of the flossing implement 10 can, once the floss held by the implement is positioned between a pair of teeth for cleaning, activate the electrical motor 68 by using the thumb switch 98. Operation of the electrical motor 68 rotates the weight 76 inside the handle 14 eccentrically about the axis 20 and vibrates the strand of floss held by the spaced-apart fingers 40. The flossing implement 10 thus allows the user to properly position the strand of floss between a pair of teeth with one hand and to impart a vibratory motion to the strand of floss for cleaning the teeth.

Various features of the invention are set forth in the following claims.

I claim:

1. A flossing implement comprising
an elongated handle having opposite ends and defining therein a cavity,
floss support means connected to and supported by said handle, said handle and floss support means vibrating without relative movement therebetween, said floss support means being adapted to have connected thereto a strand of dental floss in tension and in a position fixed relative to said handle and said floss support means, and
oscillation means in said cavity for vibrating said handle and floss support means and the strand of dental floss in unison.

2. A flossing implement as set forth in claim 1 wherein said handle includes a longitudinal axis, and wherein said oscillation means for vibrating said handle includes a weight and means for eccentrically rotating said weight about said axis.

3. A flossing implement as set forth in claim 2 wherein said means for eccentrically rotating said weight includes a selectively operable electric motor housed in said cavity and rotatably supporting said weight.

4. A flossing implement as set forth in claim 3 wherein said motor supports said weight so that the center of mass of said weight is spaced from said axis.

5. A flossing implement as set forth in claim 1 wherein said means for holding a strand of dental floss includes means defining a pair of fingers.

6. A flossing implement as set forth in claim 5 wherein said pair of fingers are spaced apart and form therebetween a space, said fingers being adapted to support the strand across the space.

7. A flossing implement as set forth in claim 1 and further including a curved neck portion extending between one opposite end of said handle and said means for supporting a strand of floss.

8. A flossing implement as set forth in claim 1 wherein said handle further includes means for storage of a supply of dental floss, said means including an opening in said handle communicable with said cavity.

9. A flossing implement comprising
an elongated, generally cylindrical handle having an axis and defining therein a cavity,
a neck portion rigidly fixed to said handle and extending from an end of said handle and curving away from said axis whereby said handle and neck portion vibrate without relative movement therebetween,
means supported by said neck portion for supporting in tension a strand of dental floss, said means for supporting a strand of dental floss including a pair of spaced-apart fingers,
a weight in said cavity,
oscillation means located in said cavity for rotating said weight about said axis and said weight being mounted eccentrically relative to said axis, said oscillation means being arranged and constructed for vibrating said handle, neck portion and floss in unison, and
means for storing a spool of dental floss in said cavity.

10. A flossing implement as set forth in claim 9 wherein said means for rotating said weight about said axis includes a selectively operable electric motor and includes a user operable switch means for connecting said motor and a source of electric current.

11. A flossing implement as set forth in claim 9 wherein said means for storing a spool of dental floss, includes an opening in said handle communicable with said cavity, and means for selectively closing said opening.

12. A flossing implement as set forth in claim 9 wherein said means for supporting a strand of dental floss includes means for supporting and guiding the strand along the contour of said fingers so that said strand extends between said spaced-apart fingers but is held in close proximity to the fingers along the length of the fingers.

13. A flossing implement as set forth in claim 12 wherein said fingers include inner ends connected to said neck portion and outer, free ends, wherein said fingers define therebetween a space, wherein each of said spaced-apart fingers has therein a groove opening away from said space and adapted for receiving such strand.

14. A flossing implement as set forth in claim 9 wherein said means for supporting in tension a strand of floss includes means on the neck portion for securing the strand of floss.

15. A flossing implement as set forth in claim 14 wherein the securing means is located adjacent the fingers.

16. A flossing implement as set forth in claim 14 wherein the securing means includes a knob around which the strand can be securely wrapped.

17. A flossing implement comprising
a first generally semi-cylindrical shell,
a second generally semi-cylindrical shell,
means for releasably fastening said first and second shells to form an elongated, generally cylindrical handle having opposite ends and a longitudinal axis, said handle defining therein a cavity,
a portion of said cavity adapted to house a spool of dental floss,
means for vibrating said handle including an electric motor located in said cavity and rotatably supporting a weight for rotation about said axis, said weight being mounted eccentrically relative to said axis,
means for affording access to said cavity including an opening extending through at least one of said first and second shells and located adjacent said portion of said cavity adapted to house the spool,
user actuable switch means for operably connecting said electric motor with a source of current, and
means extending from one of said opposite ends for supporting a strand of dental floss in tension, said means for vibrating said handle, said handle, and said means for supporting a strand of floss being arranged and constructed so that said handle and said floss vibrate in unison.

18. A flossing implement as set forth in claim 17 wherein said means for supporting a strand of dental floss includes a neck portion extending from said opposite one end generally parallel to said axis, said neck having a portion diverging from said axis and terminating in a pair of spaced-apart fingers, said pair of fingers adapted to support therebetween a strand of floss.

19. A flossing implement as set forth in claim 18 wherein said pair of fingers form therebetween a V-shaped space having a sufficient width to provide clearance on either side of a row of teeth, and wherein said fingers support the strand of dental floss so that the strand extends across said space.

20. A flossing implement as set forth in claim 19 wherein each of said pair of fingers has therein a groove adapted to receive a strand of dental floss.

21. A flossing implement as set forth in claim 17 wherein said source of current is a battery and wherein a second portion of said cavity is adapted to house said battery.

22. A flossing implement as set forth in claim 21 wherein said means affording access to said battery includes a second opening in said other opposite end adapted to receive said battery, and further including a removable cap for closing said second opening.

23. A flossing implement as set forth in claim 22 wherein said user actuable switch means includes spring means on said cap for contacting said battery.

* * * * *